United States Patent [19]

Burress

[11] Patent Number: 4,822,943

[45] Date of Patent: Apr. 18, 1989

[54] PRODUCTION OF PARA-DIISOPROPYLBENZENE

[75] Inventor: George T. Burress, Bridgewater, N.J.

[73] Assignee: Mobil Oil Corporation, New York, N.Y.

[21] Appl. No.: 748,883

[22] Filed: Jun. 26, 1985

Related U.S. Application Data

[63] Continuation of Ser. No. 568,012, Jan. 4, 1984, abandoned, which is a continuation-in-part of Ser. No. 429,600, Sep. 30, 1982, Pat. No. 4,469,908, which is a continuation of Ser. No. 969,630, Dec. 14, 1978, abandoned.

[51] Int. Cl.$^4$ ............................................... C07C 2/68
[52] U.S. Cl. ................................................... 585/467
[58] Field of Search ......................................... 585/467

[56] References Cited

U.S. PATENT DOCUMENTS

| | | | |
|---|---|---|---|
| 3,393,262 | 7/1983 | Kaeding | 585/467 |
| 4,049,737 | 9/1977 | Dwyer et al. | 585/467 |
| 4,086,287 | 4/1978 | Kaeding et al. | |
| 4,117,026 | 9/1978 | Haag et al. | 585/467 |
| 4,230,894 | 10/1980 | Young. | |
| 4,329,509 | 5/1982 | Haag et al. | 568/768 |
| 4,387,259 | 6/1983 | Barile | 585/467 |
| 4,418,235 | 11/1983 | Haag et al. | 585/467 |
| 4,421,941 | 12/1983 | Olson et al. | 585/467 |
| 4,434,305 | 2/1984 | Kurosaka et al. . | |
| 4,447,666 | 5/1984 | McWilliams | 585/467 |
| 4,469,908 | 9/1984 | Burress | 585/467 |

FOREIGN PATENT DOCUMENTS 0012514  6/1980  European Pat. Off. ............ 585/467

OTHER PUBLICATIONS

Khadzhier et al., Chem. Abst., vol. 97, #5869C (1982).

*Primary Examiner*—Curtis R. Davis
*Attorney, Agent, or Firm*—Alexander McKillop; Charles J. Speciale; Edward F. Kenehan, Jr.

[57] ABSTRACT

A process is disclosed whereby cumene and/or benzene is brought into contact propylene in the presence of a ZSM-12 catalyst to selectively produce para-diisopropylbenzene.

1 Claim, No Drawings

PRODUCTION OF PARA-DIISOPROPYLBENZENE

CROSS-REFERENCE TO RELATED APPLICATION

This application is a continuation of U.S. Application Ser. No. 568,012, filed Jan. 4, 1984, and now abandoned which is a continuation-in-part of U.S. Application Ser. No. 429,600 filed Sept. 30, 1982, now U.S. Pat. No. 4,469,908, which is a continuation of U.S. Application Ser. No. 969,630, filed Dec. 14, 1978, now abandoned.

BACKGROUND

This invention relates to a process for the selective production of para-diisopropylbenzene by catalytic propylation of cumene and/or benzene in the presence of a particular crystalline zeolite catalyst designated as ZSM-12.

Para-diisopropylbenzene has been used for a number of purposes, e.g.; as solvents and chemical intermediates.

Alkylation of aromatic hydrocarbons utilizing crystalline zeolite catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom unit. U.S. Pat. No. 3,251,897 to Wise describes alkylation of aromatic hydrocarbons in the presence of X- or Y-type crystalline zeolites, specifically such type zeolites wherein the cation is rare earth and/or hydrogen. U.S. Pat. No. 3,751,504 to keown et al and U.S. Pat. No. 3,751,506 to Burress describe vapor phase alkylation of aromatic hydrocarbons with olefins in the presence of a specified type of zeolite catalyst.

U.S. Pat. No. 3,755,483 to Burress discloses vapor phase alkylation of aromatic hydrocarbons in the presence of ZSM-12 zeolite catalyst. The reaction is carried out at temperatures between the critical temperature of the aromatic compound and 482° C. (900° F.). The critical temperature and pressure of benzene are 288.9° C. (552° F.) and 48.6 atm. (4.9×$10^6$ N/M²).

Harper et al have described the catalytic alkylation of benzene with propylene over a crystalline zeolite (*Petrochemical Preprints*, American Chemical Society, Vol. 22, No. 3, p. 1084, 1977). Extensive kinetic and catalyst aging studies were conducted with a rare earth-exchanged Y-type zeolite (REY) catalyst.

U.S. Pat. No. 4,393,262 to Kaeding describes a process whereby benzene is brought in contact with ZSM-12 to selectively produce isopropylbenzene (i.e. cumene). This process may be carried out in the liquid or the vapor phase at temperatures of from about 100° C. to about 300° C. and pressure ranging from $10^5$ N/m² to 6×$10^6$ N/m².

The entire disclosures of the above-identified U.S. patents are expressly incorporated herein by reference.

SUMMARY

In accordance with one aspect of the present invention, there is provided a process for the selective propylation of cumene with the selective production of para-diisopropylbenzene, said process comprising contacting mixtures of cumene and propylene with a ZSM-12 catalyst under sufficient propylation conditions.

In accordance with another aspect of the invention, there is provided a process for the selective production of para-diisopropylbenzene, said process comprising the steps of:

(i) contacting mixtures of benzene and propylene with a ZSM-12 catalyst under sufficient propylation conditions to selectively produce cumene; and (ii) contacting mixtures of said cumene of step (i) and propylene with a ZSM-12 catalyst under sufficient propylation conditions.

In accordance with another aspect of the invention, there is provided a process for the propylation of benzene with selective production of para-diisopropylbenzene, said process comprising contacting mixtures of benzene and propylene with a ZSM-12 catalyst under sufficient propylation conditions wherein the molar ratio of propylane to benzene is at least 2.

DESCRIPTION OF SPECIFIC EMOBIDMENTS

The crystalline zeolites utilized herein are members of a novel class of zeolites that exhibits unusual properties. Although these zeolites have unusually low alumina contents, i.e. high silica to alumina rations, they are very active when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of stem at high temperature which induces irreversible collapse of the framework of other zeolites, e.g., of the X and A type. Furthermore, carbonaceous deposits, when formed, may be removed by controlled burning at higher than usual temperatures to restore activity. These zeolites, used as catalysts, generally have low coke-forming activity and, therefore, are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linda A and the large pore Linde X, i.e. the pore windows of the structure have about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in some instances excessive puckering of the rings or pore blockage may render these zeolites ineffective.

Although it is thought that 12-membered rings usually do not offer sufficient constraint to produce advantageous conversions, it is noted that the puckered 12-ring structure of TMA offretite shows constrained access. Other 12-ring structures may exist which may be operative and it is not the intention to judge the usefulness herein of a particular zeolite merely from theoretical structural considerations.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constant for the two hydrocarbons. Zeolites suitable for the present invention are those having a Constraint Index of 1 to 12. Constraint Index (C.I.) values for some typical zeolites are:

| ZEOLITE | C.I. |
|---|---|
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 1.5 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produced a value of the Constraint Index slightly less than 1, e.g. 0.9, or somewhat greater than 12, e.g., 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this special class of zeolite.

More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, streaming, alumina extraction and calcination, in combinations. Natural minerals which may be treated include ferrierite, brewsterite, stilbite, dachiardite, epistilbite, heulandite, and clinoptilolite.

Of the zeolite materials described by the above parameters, it has been found that ZSM-12 is especially useful in the hereindisclosed process. Said ZSM-12 is, therefore, particularly preferred in the practice of the present invention.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on Page 19 of the article of Zeolite Structure by W. M. Meier. This paper, the entire contents of which are incorporated herein by reference, is included in "Proceedings of the Conference on Molecular Sieves, London, April 1967," published by the Society of Chemical Industry, London 1968.

When the crystal structure in unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| ZEOLITE | VOID VOLUME | FRAMEWORK DENSITY |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.54 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired alkylation process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

A second optional component of the aromatics conversion catalysts prepared in accordance with the present invention comprises a minor proportion, e.g., from about 0.05% to 50% by weight of the catalyst composite, of a difficultly reducible oxide. Oxides of this type can include oxides of phosphorus as well as those oxides of the metals of Groups IA, IIA, IIIA, IVA, VA, VIA, VIIA, VIIIA, IB, IIB, IIIB, IVB, OR VB of the Periodic Chart of the Elements (Fisher Scientic Company, Catalog No. 5-702-10) which serve to enhance the para-selectivity properties of the catalysts modified therewith. The difficultly reducible oxides most commonly employed to modify the selectivity properties of the zeolite-based catalysts herein are oxides of phosphorus and magnesium. Thus, the catalysts prepared herein can be treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such catalysts at least in part in the form of phosphorus oxide in an amount of from about 0.25% to about 25% by weight of the catalyst composition, preferably from about 0.7% to about 15% by weight. Such incorporation can be readily effected by contacting the zeolite composite with a solution of an appropriate phosphorus compound, followed by drying and calcining to convert phosphorus in the zeolite to its oxide form. Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3-5 hours but may be extended to 24 hours or longer.

Magnesium oxide is another preferred difficultly reducible oxide which can be incorporated with the zeolite composites in a manner similar to that employed with phosphorus. Magnesium can comprise from about 0.25% to 25% by weight preferably from about 1% to 15% by weight present at least in part as magnesium oxide. As with phosphorus, magnesium oxide incorporaiton is effected by contacting the zeolite composite with an appropriate magnesium compound followed by drying and calcining to convert magnesium in the zeolite to its oxide form. Preferred magnesium-containing compounds include magnesium nitrate and magnesium acetate. Calcination times and temperatures are generally the same as recited hereinbefore for calcination of phosphorus-containing catalysts.

In addition to treatment of the zeolite composites to incorporate phosphorus and/or magnesium oxides as hereinbefore described in detail, such zeolites may also be modified in a substantially similar manner to incorporate thereon a variety of other oxide materials to enhance para-selectivity. Such oxide materials include oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group IVB metals (U.S. Pat. No. 4,278,827); Group VIA metals (U.S. Pat. No. 4,259,537); Group IA elements (U.S. Pat. No. 4,329,533); cadmium (U.S. Pat. No. 4,384,155); iron and/or cobalt (U.S. Pat. No. 4,380,685); Group IIIB metals (U.S. Pat. No. 4,276,437); Group IVA metals (U.S. Pat. No. 4,302,620); Group VA metals (U.S. Pat. No. 4,302,621); and Group IIIA elements (U.S. Pat. No. 4,302,622).

As pointed out in the aforementioned U.S. Pat. No. 4,393,262, cumene may be produced by the propylation of benzene in the presence of the above-described catalyst by contact of the benzene with propylene at a temperature between about 100° C. and 250° C. The reaction generally takes place at atmospheric pressure, but the pressure may be within the approximate range of $10^5$ $N/m^2$ to $6 \times 10^6$ $N/m^2$ (1 atm to 60 atm). The molar ratio of benzene to propylene is preferably within the approximate range of 12:1 to 1:1. The reaction may be suitably accomplished utilizing a feed weight hourly space velocity (WHSV) of between about 0.5 and about 100, preferably between about 5 and about 40.

Propylation of cumene to produce paradiisopropylbenzene may be carried out under conditions analogous to those described hereinabove for producing cumene. More particularly, para-diisopropylbenzene may be produced by the propylation of cumene in the presence of the above-described catalyst by contact of the cumene with propylene at a temperature between about 100° C. and about the critical temperature, and preferably between about 150° C. and 250° C. The reaction generally takes place at atmospheric pressure, but the pressure may be within the approximate range of $10^5$ $N/m^2$ to $6 \times 10^6$ $N/m^2$ (1 atm to 60 atm). The molar ratio of cumene to propylene is preferably within the approximate range of 12:1 to 1:1. The reaction may be suitably accomplished utilizing a feed weight hourly space velocity (WHSV) of between about 0.5 and about 100, preferably between about 5 and about 40.

By means of the process of the present invention, it is possible to obtain a diisopropylbenzene product having, e.g., at least 80 of the para-isomer and, e.g., less than 1 percent of the ortho-isomer.

The process of this invention may be conducted with the organic reactants in either the gaseous or the liquid phase or both. It may be carried out as a batch-type, semi-continuous or continuous operation utilizing a fixed, fluidized or moving bed catalyst system. The Examples which follow will serve to illustrate the process of this invention without being limiting thereon.

When Alpha Value is mentioned in these Examples, it is noted that the Alpha Value is an approximate indication of the catalytic cracking activity of the catalyst compared to a standard catalyst and it gives the relative rate constant (rate or normal hexane conversion per volume of catalyst per unit time). It is based on the activity of the highly active silica-alumina cracking catalyst taken as an Alpha Value of 1 (Rate Constant=0.016 sec$^{-1}$). The Alpha Test is described in U.S. Pat. No. 3,354,078 and in The Journal of Catalysis, Vol. IV, pp. 522-529 (August 1965), both incorporated herein by reference as to that description.

In the Examples which follow, the catalytic, vapor phase alkylation unit was constructed entirely of 316 or 321 stainless steel. The reactor dimensions were 1¼ inch od, ⅝ inch id ×21⅜ inches long and rated to operate at 5000 psig at 650° F. It was fitted with a metal, spiral insert in the top section which functioned as the preheater. The catalyst section contained a ⅛ inch centered thermowell. A three zone furnace with independent controls was used to obtain the desired temperature. Six or nine grams, 12-28 cc's, of the catalyst was centered in the middle zone with low surface area quartz chips to prevent void spaces.

Standard equipment such as pumps (Milton-Roy), temperature, pressure and flow control devices, feed and storage tanks, etc. were selected and designed to operate continuously and unattended for at least 24-hour periods. The propylene was stored in the liquid phase in a Jergeson gauge. Accurate metering to the reactor was supplied by two Isco pumps which could be operated individually or together. This provided flexibility to operate continuously for 24 hours and permit uninterrupted flow while the pump cylinders were refilled. Automatic detector and shut-off devices were installed in the event of a power failure. The entire unit was located in a large hood.

The liquid product was condensed with water cooling. The remaining gas was collected in a dry gas collecting tower with a mercury seal float. Liquid and gaseous compositions were analyzed by standard g.c. techniques. A ⅛"×12' column containing 60–80 mesh silica gel, was used for the gas analysis. A 150'×0.01" od Perkin-Elmer, OS-138-polyphenyl ether capillary column was used for analysis of the liquid product. In order to determine the ortho/meta/para ratio of diisopropylbenzene (DIPB) product, a 50 meter, Chrompac fused silica column coated with CP-Wax CB was used for the liquid product.

Each of the ZSM-12 catalysts of the Examples which follow were intimately mixed with 35 wt.% alumina binder, then pressed into wafers, crushed and screened to a uniform particle size of 14–20 mesh.

EXAMPLE 1

The ZSM-12 catalyst employed in this Example was a hydrogen form of ZSM-12 (i.e. HZSM-12) having a silica to alumina ratio of 213 and an Alpha Value of 39. The zeolite was calcined in $N_2$ in the absence of binder, $NH_4+$ ion exchanged then compounded with alumina and extruded, followed by drying and final calcination.

Conditions of reaction and a summary of analytical results are shown in Table 1 wherein "CU" stand for cumene, "NPRBZ" stands for n-propylbenzene and "Other" represents primarily propylene oligomers. The ratio of para/meta DIPB isomers produced ranged from 76/23 at 175° C. to 47/53 at 250° C.

EXAMPLE 2

The HZSM-12 catalyst of this Example was essentially equivalent to that of Example 1 except that it was prepared in a slightly different manner. More particularly, the same zeolite as Example 1 was processed by the sequence of extruding, calcining, $NH_4+$ exchange, drying and final calcination. The composition of the catalyst was the same as the composition of the catalyst of Example 1.

Conditions of reaction and a summary of analytical results are shown in Table 2, wherein "CU" stands for cumene, "NPRBZ" stands for n-propylbenzene and "Other" represents primarily propylene oligomers.

TABLE 2

Alkylation of Cumene with Propylene to Produce Diisopropylbenzene

| Run No. | 1 | 2 | 3 | 4 | 5 | 6 |
|---|---|---|---|---|---|---|
| Temp., °C. | 150 | 200 | 250 | 300 | 250 | 300 |
| Pressure, psig | 0 | 0 | 0 | 0 | 0 | 0 |
| CU/C₃H₆ | | | | | | |
| WHSV | 7.2/.9 | 7.2/.9 | 7.2/.9 | 7.2/.9 | 13.9/1.7 | 13.9/1.7 |
| Mole | 2.9/1 | 2.9/1 | 2.9/1 | 2.9/1 | 2.8/1 | 2.8/1 |
| Conversion, wt % | | | | | | |
| CU | 13.4 | 17.2 | 26.9 | 40.7 | 16.6 | 33.9 |
| C₃H₆ | 27.5 | 48.0 | 76.7 | 47.0 | 45.3 | 50.8 |
| Selectivity, wt % | | | | | | |
| Benzene | 11.0 | 1.5 | 4.3 | 25.4 | 3.8 | 17.9 |
| DIPB | | | | | | |
| para | 67.4 | 74.2 | 49.1 | 20.0 | 66.2 | 27.5 |
| meta | 18.6 | 20.7 | 41.1 | 40.8 | 25.3 | 45.6 |
| ortho | .9 | .5 | .2 | .2 | .15 | .1 |
| Total | 86.9 | 95.4 | 90.4 | 61.0 | 91.7 | 73.2 |
| NPRBZ | 0 | 0 | .06 | .68 | 0 | .36 |
| Other | 2.1 | 3.1 | 5.2 | 12.9 | 4.5 | 8.5 |
| DIPB % | | | | | | |
| para | 77.6 | 77.7 | 54.3 | 32.8 | 72.2 | 37.5 |
| meta | 21.4 | 21.7 | 45.4 | 66.9 | 27.6 | 62.3 |
| ortho | 1.0 | .6 | .3 | .3 | .2 | .2 |

EXAMPLE 3

The ZSM-12 catalyst employed in this Example was an HZSM-12 catalyst having a silica to alumina ratio of 180. The hydrogen form of the zeolite was prepared by calcination, $NH_4+$ ion exchange and final calcination.

TABLE 1

Alkylation of Cumene with Propylene to Produce Diisopropylbenzene

| Run No. | 1 | 2 | 3 | 4 | 5 | 6 | 7 | 8 |
|---|---|---|---|---|---|---|---|---|
| Temperature, °C. | 175 | 200 | 22 | 250 | 175 | 200 | 225 | 250 |
| Pressure, psig | 0 | 0 | 0 | 0 | 0 | 0 | 0 | 0 |
| CU/C₃H₆ | | | | | | | | |
| WHSV | 6.8/.87 | 7.6/.87 | 7.7/.87 | 6.71/.87 | 14.3/.85 | 14.5/.85 | 14.9/.85 | 13.8/.85 |
| mole | 2.7/1 | 3.1/1 | 3.1/1 | 2.7/1 | 5.9/1 | 6.0/1 | 6.2/1 | 5.7/1 |
| Conversion, wt % | | | | | | | | |
| CU | 18 | 26 | 29 | 36 | 8 | 13 | 15 | 19 |
| C₃H₆ | 68 | 70 | 82 | 89 | 51 | 65 | 79 | 85 |
| Selectivity, % | | | | | | | | |
| Benzene | 2.2 | 1.2 | 1.3 | 3.3 | .9 | .7 | 1.7 | 4.8 |
| DIPB | | | | | | | | |
| para | 69.6 | 68.6 | 62.3 | 42.6 | 72.1 | 71.7 | 63.0 | 47.4 |
| meta | 21.0 | 23.1 | 31.3 | 47.8 | 22.9 | 23.9 | 32.0 | 44.0 |
| ortho | 1.4 | .9 | .4 | .3 | 1.4 | .8 | .4 | .3 |
| Total | 92.0 | 92.6 | 94.0 | 90.7 | 96.4 | 96.4 | 95.4 | 91.7 |
| NPRBZ | 0 | 0 | 0 | 0 | 0 | 0 | 0 | 0 |
| Other | 5.8 | 6.2 | 4.7 | 6.0 | 2.7 | 2.9 | 2.9 | 3.5 |
| DIPB % | | | | | | | | |
| para | 75.7 | 74.1 | 66.3 | 47.0 | 75.4 | 74.3 | 66.0 | 51.7 |
| meta | 22.8 | 29.4 | 33.3 | 52.7 | 23.1 | 24.8 | 33.6 | 48.0 |
| ortho | 1.5 | 1.0 | .4 | .3 | 1.5 | .8 | .4 | .3 |

The catalyst was steamed for 7 hours at 1000° F., 100 percent steam and 0 psig. The catalyst had an Alpha Value of 30.

Conditions of reaction and a summary of analytical results are shown in Table 3, wherein "CU" stands for cumene, "NPRBZ" stands for n-propylbenzene and "Other" represents primarily propylene oligomers.

TABLE 3

Alkylation of Cumene with Propylene to Produce Diisopropylbenzene

| Run No. | 1 | 2 | 3 | 4 | 5 | 6 |
|---|---|---|---|---|---|---|
| Temp., °C. | 150 | 200 | 250 | 300 | 250 | 300 |
| Pressure, psig | 0 | 0 | 0 | 0 | 0 | 0 |
| CU/C$_3$H$_6$ | | | | | | |
| WHSV | 7.1/.85 | 7.1/.85 | 7.1/.85 | 7.1/.85 | 14.4/1.65 | 14.4/1.65 |
| Mole | 2.9/1 | 2.9/1 | 2.9/1 | 2.9/1 | 3.1/1 | 3.1/1 |
| Conversion, wt % | | | | | | |
| CU | 7.8 | 7.2 | 10.7 | 33.1 | 15.7 | 30.2 |
| C$_3$H$_6$ | 40.0 | 47.3 | 63.9 | 53.2 | 73.3 | 50.4 |
| Selectivity, wt % | | | | | | |
| Benzene | 3.0 | 1.3 | 3.2 | 27.6 | 1.6 | 14.9 |
| DIPB | | | | | | |
| para | 66.4 | 76.0 | 61.5 | 20.7 | 69.1 | 31.5 |
| meta | 20.0 | 16.8 | 26.4 | 36.3 | 24.6 | 45.2 |
| ortho | 3.9 | .9 | .3 | .3 | .2 | .3 |
| Total | 90.3 | 93.7 | 88.2 | 57.3 | 93.3 | 77.0 |
| NPRBZ | .01 | .01 | .01 | 0 | 0 | 0 |
| Other | 6.7 | 5.0 | 8.6 | 14.8 | 4.5 | 8.1 |
| DIPB % | | | | | | |
| para | 73.5 | 81.1 | 69.7 | 36.2 | 73.5 | 40.9 |
| meta | 22.1 | 17.9 | 29.9 | 63.3 | 26.2 | 58.8 |
| ortho | 4.4 | 1.0 | .4 | .5 | .3 | .3 |

EXAMPLE 4

The ZSM-12 catalyst of this Example was a magnesium modified catalyst (i.e. Mg-ZSM-12) prepared by impregnating the unsteamed catalyst of Example 3 with aqueous magnesium nitrate. This impregnated catalyst was filtered, dried and calcined in air in a shallow dish in a furnace by slowly increasing the temperature from 30–500° C. over 1.5 hours and standing overnight at 500° C. The resulting Mg-ZSM-12 contained 2.3 weight percent of Mg.

Conditions of reaction and a summary of analytical results are shown in Table 4, wherein "CU" stands for cumene, "NPRBZ" stands for n-propylbenzene and "Other" represents primarily propylene oligomers.

TABLE 4

Alkylation of Cumene with Propylene to Produce Diisopropylbenzene

| Run No. | 1 | 2 | 3 | 4 | 5 |
|---|---|---|---|---|---|
| Temp., °C. | 150 | 200 | 250 | 300 | 300 |
| Pressure, psig | 0 | 0 | 0 | 0 | 0 |
| CU/C$_3$H$_6$ | | | | | |
| WHSV | 7.2/.85 | 7.2/.85 | 7.2/.85 | 7.2/.85 | 7.2/.85 |
| Mole | 3.1 | 3.1 | 3.1 | 3.1 | 3.1 |
| Conversion, wt % | | | | | |
| CU | 4.4 | 4.2 | 10.4 | 23.6 | 29.2 |
| C$_3$H$_6$ | 8.3 | 9.0 | 68.7 | 42.0 | 46.6 |
| Selectivity, wt % | | | | | |
| Benzene | 7.6 | 2.6 | 2.9 | 23.1 | 10.2 |
| DIPB | | | | | |
| para | 70.9 | 77.5 | 68.3 | 28.2 | 35.3 |
| meta | 16.4 | 16.1 | 23.4 | 37.5 | 36.5 |
| ortho | .65 | .48 | .29 | .35 | .45 |
| Total | 88.0 | 94.1 | 92.0 | 66.1 | 72.3 |
| NPRBZ | .69 | .38 | .13 | 0 | 0 |
| Other | 3.7 | 2.9 | 5.0 | 10.8 | 17.5 |
| DIPB % | | | | | |
| para | 80.7 | 82.4 | 74.3 | 42.7 | 48.8 |
| meta | 18.6 | 17.1 | 25.4 | 56.8 | 50.5 |
| ortho | .7 | .5 | .3 | .5 | .6 |

EXAMPLE 3

The ZSM-12 catalyst of this Example was a catalyst modified with both phosphorous and magnesium (i.e. P-Mg-ZSM-12) prepared by first treating the unsteamed catalyst of Example 3 with magnesium in accordance with the general procedure of Example 4 and then by treating with phosphorous. The phosphorous treating procedure was essentially equivalent to the magnesium treating procedure except that the catalyst was impregnated with aqueous diammonium acid phosphate (DAAP). The resulting P-Mg-ZSM-12 catalyst contained 5.4 weight percent P and 0.2 weight percent Mg.

Conditions of reaction and a summary of analytical results are shown in Table 5, wherein "CU" stands for cumene, "NPRBZ" stands for n-propylbenzene and "Other" represents primarily propylene oligomers.

TABLE 5

Alkylation of Cumene with Propylene to Produce Diisopropylbenzene

| Run No. | 1 | 2 | 3 | 4 |
|---|---|---|---|---|
| Temp., °C. | 150 | 200 | 250 | 300 |
| Pressure, psig | 0 | 0 | 0 | 0 |
| CU/C$_3$H$_6$ | | | | |
| WSHV | 3.4 | 3.4 | 3.4 | 3.4 |
| Mole | 3/1 | 3/1 | 3/1 | 3/1 |
| Conversion, wt % | | | | |
| CU | tr$^a$ | tr | tr | 4.0 |
| C$_3$H$_6$ | 28 | 29 | 27 | 15 |
| Selectivity, wt % | | | | |
| Benzene | 34.5 | 15.2 | 7.1 | 19.0 |
| DIPB | | | | |
| para | 23.8 | 52.6 | 66.1 | 54.4 |
| meta | 15.5 | 8.7 | 11.1 | 14.7 |
| ortho | 0 | 0 | 0 | .3 |
| Total | 39.3 | 61.3 | 77.2 | 69.4 |
| NPRBZ | 3.1 | 2.8 | .05 | .02 |
| Other | 23.1 | 20.7 | 15.6 | 11.6 |
| DIPB % | | | | |
| para | 60.5 | 85.8 | 85.7 | 78.3 |
| meta | 39.5 | 14.2 | 14.3 | 21.2 |
| ortho | 0 | 0 | 0 | .5 |

$^a$Trace amounts detected.

EXAMPLE 6

The ZSM-12 catalyst of this Example was a phosphorous modified catalyst (i.e. P-ZSM-12) prepared by impregnating the unsteamed catalyst of Example 3 with aqueous diammonium acid phosphate. This impregnated catalyst was filtered, dried and calcined in air in a shallow dish in a furnace by slowly increasing the temperature from 30–500° C. over 1.5 hours and standing overnight at 500° C. The resulting P-ZSM-12 contained 2.69 weight percent of P.

Conditions of reaction and a summary of analytical results are shown in Table 6, wherein "CU" stands for cumene, "NPRBZ" stands for n-propylbenzene and "Other" represents primarily propylene oligomers.

TABLE 6

Alkylation of Cumene with Propylene to Produce Diisopropylbenzene

| Run No. | 1* | 2 | 3* | 4 | 5 | 6 |
|---|---|---|---|---|---|---|
| Temp., °C. | 150 | 200 | 200 | 250 | 250 | 300 |
| Pressure, psig | 0 | 0 | 0 | 0 | 0 | 0 |
| CU/C$_3$H$_6$ | | | | | | |
| WHSV | 7.3/.83 | 7.3/.83 | 7.3/.85 | 7.3/.83 | 7.3/.85 | 7.3/.85 |
| Mole | 3.1/1 | 3.1/1 | 3.0/1 | 3.1/1 | 3.0/1 | 3.0/1 |
| Conversion, wt % | | | | | | |
| CU | .9 | 1.3 | 5.8 | 5.6 | 10.8 | 23.0 |
| C$_3$H$_6$ | 19.2 | 12.7 | 59.1 | 23.5 | 96.9 | 35.4 |
| Selectivity, wt % | | | | | | |
| Benzene | 0 | 19.0 | .5 | 4.7 | 3.0 | 23.0 |
| DIPB | | | | | | |
| para | 71.8 | 57.9 | 74.8 | 72.0 | 61.9 | 26.7 |
| meta | 21.6 | 13.1 | 19.5 | 19.6 | 29.6 | 34.2 |
| ortho | 3.2 | 0 | 1.3 | .5 | .5 | .3 |
| Total | 96.6 | 71.0 | 95.6 | 92.1 | 92.0 | 61.2 |
| NPRBZ | 0 | 1.21 | .15 | .31 | .10 | .57 |
| Other | 3.4 | 8.8 | 3.7 | 2.9 | 4.9 | 15.2 |
| DIPB % | | | | | | |
| para | 74.3 | 81.5 | 78.3 | 78.1 | 67.3 | 43.6 |
| meta | 22.4 | 18.5 | 20.4 | 21.3 | 32.2 | 55.9 |
| ortho | 3.3 | 0 | 1.3 | .6 | .5 | .5 |

*calcined before use

EXAMPLE 7

The ZSM-12 catalyst of this Example was prepared in the same manner as the catalyst of Example 3 except that it was steamed for 3 hours instead of 7 hours. The Alpha Value of this catalyst was not determined.

Conditions of reaction and a summary of analytical results are shown in Table 7, wherein "CU" stands for cumene, "NPRBZ" stands for n-propylbenzene and "Other" represents primarily propylene oligomers.

TABLE 7

Alkaylation of Cumene with Propylene to Produce Diisopropylbenzene

| Run No. | 1 | 2 | 3 | 4 | 5* | 6 | 7 | 8 |
|---|---|---|---|---|---|---|---|---|
| Temperature, °C. | 150 | 150 | 150 | 200 | 200 | 200 | 250 | 250 |
| Pressure, psig | 500 | 500 | 500 | 500 | 500 | 500 | 500 | 500 |
| CU/C$_3$H$_6$ | | | | | | | | |
| WHSV | 7.1/.84 | 7.1/.84 | 7.1/.84 | 7.1/.84 | 7.4/.83 | 13.8/.83 | 13.3/.83 | 7.3/.83 |
| mole | 2.9/1 | 2.9/1 | 2.9/1 | 2.9/1 | 3.1/1 | 5.8/1 | 5.8/1 | 3.1/1 |
| Conversion, wt % | | | | | | | | |
| CU | 11.1 | 10.5 | 8.2 | 17.9 | 9.1 | 11.0 | 19.1 | 32.2 |
| C$_3$H$_6$ | 96.5 | 71.8 | 46.8 | 88.8 | 100 | 97 | 99 | 99 |
| Selectivity, % | | | | | | | | |
| Benzene | .5 | 1.5 | .5 | .5 | .1 | .2 | 4.9 | 6.1 |
| DIPB | | | | | | | | |
| para | 66.4 | 61.9 | 60.3 | 65.8 | 68.9 | 71.8 | 57.3 | 42.5 |
| meta | 18.1 | 17.8 | 17.5 | 16.9 | 18.4 | 18.1 | 27.6 | 32.8 |
| ortho | 2.7 | 2.8 | 2.6 | 1.5 | 1.3 | 1.4 | .5 | .6 |
| Total | 87.2 | 82.5 | 80.4 | 84.2 | 88.6 | 91.3 | 85.4 | 77.9 |
| NPRBZ | .18 | .80 | .88 | .23 | .84 | .49 | .16 | .12 |
| Other | 12.1 | 15.2 | 18.2 | 15.1 | 10.5 | 18.10 | 9.5 | 15.8 |
| DIPB % | | | | | | | | |
| para | 76.2 | 75.1 | 74.9 | 78.2 | 77.7 | 78.7 | 67.1 | 54.5 |
| meta | 20.8 | 21.5 | 21.8 | 20.0 | 20.8 | 19.8 | 32.3 | 44.7 |
| ortho | 3.0 | 3.4 | 3.3 | 1.8 | 1.5 | 1.5 | 0.6 | .8 |

*Calcine 18 hrs. before making run.

With regard to the foregoing Examples, it is noted that the runs set forth in Example 7 were carried out at a pressure of 500 psig. The remainder were made at atmospheric pressure. The temperature range varied from 150–300° C. The weight hourly space velocity varied from about 8–15 and the molar cumene/propylene feed ratio varied from about 3/1 to 6/1.

In order to demonstrate the effect of pressure, data from Tables 1, 2 and 7 are summarized in Table 8. This data corresponds to the catalysts of Examples 1, 2 and 7, which are each similar but not identical acid forms of ZSM-12.

TABLE 8

Alkylation of Cumene with Propylene to Produce Diisopropylbenzene
Effect of Pressure

| Table No. | 7 | 2 | 7 | 2 | 1 | 7 | 2 | 1 |
|---|---|---|---|---|---|---|---|---|
| Run No. | 1 | 1 | 4 | 2 | 2 | 8 | 3 | 4 |
| Temperature, °C. | 150 | 150 | 200 | 200 | 200 | 250 | 250 | 250 |
| Pressure, psig | 500 | 0 | 500 | 0 | 0 | 500 | 0 | 0 |
| CU/C$_3$H$_6$ | | | | | | | | |
| WHSV | 7.1/.8 | 7.2/.9 | 7.2/.9 | 7.2/.9 | 7.6/.87 | 7.2/.9 | 7.2.9 | 6.7/.87 |
| mole | 2.9/1 | 2.9/1 | 2.9/1 | 2.9/1 | 3.1/1 | 2.9/1 | 2.9/1 | 2.7/1 |
| Conversion, wt % | | | | | | | | |
| CU | 11.1 | 13.4 | 17.9 | 17.2 | 26 | 32.2 | 26.9 | 36 |
| C$_3$H$_6$ | 96.5 | 27.5 | 88.8 | 48.0 | 70 | 99 | 76.7 | 89 |
| Selectivity, % | | | | | | | | |
| Benzene | 5 | 11.0 | .5 | 1.5 | 1.2 | 6.1 | 4.3 | 3.3 |
| DIPB | | | | | | | | |
| para | 66.4 | 67.4 | 65.8 | 74.2 | 68.6 | 42.5 | 49.1 | 42.6 |

TABLE 8-continued

Alkylation of Cumene with Propylene to Produce Diisopropylbenzene
Effect of Pressure

| | Table No. 7 | Table No. 2 | Table No. 7 | Table No. 2 | Table No. 1 | Table No. 7 | Table No. 2 | Table No. 1 |
|---|---|---|---|---|---|---|---|---|
| | Run No. 1 | Run No. 1 | Run No. 4 | Run No. 2 | Run No. 2 | Run No. 8 | Run No. 3 | Run No. 4 |
| meta | 18.1 | 18.6 | 16.9 | 20.7 | 23.1 | 34.8 | 41.1 | 47.8 |
| ortho | 2.7 | .9 | 1.5 | .5 | .9 | .6 | .2 | .3 |
| Total | 87.2 | 86.9 | 84.2 | 95.4 | 92.6 | 77.9 | 90.0 | 90.7 |
| NPRBZ | .18 | 0 | .23 | 0 | 0 | .12 | .06 | 0 |
| Other | 12.1 | 2.1 | 15.1 | 3.1 | 6.2 | 15.8 | 5.2 | 6.0 |
| DIPB % | | | | | | | | |
| para | 76.2 | 78.2 | 77.7 | 74.1 | 54.5 | 54.3 | 47.0 | |
| meta | 20.8 | 21.4 | 20.0 | 21.7 | 29.4 | 44.7 | 45.4 | 52.7 |
| ortho | 3.0 | 1.0 | 1.8 | .6 | 1.0 | .8 | .3 | .3 |

At 500 psig, Table 7, the reaction was primarily in liquid/solid heterogeneous phases. By contrast, at 0 psig it was a heterogeneous gas/solid reaction, Tables 1 and 2. Examination of the data indicates that (a) cumene conversions were similar at 0 and 500 psig, (b) propylene conversion was significantly higher at 500 psig, (c) the selectivity to DIPB was highest at 0 psig, (d) less n-propylbenzene was made at 0 psig, (e) signficantly less by-products were made at 0 psig, and (f) less ortho-DIPB was made at 0 psig.

In summary, better overall performance was observed at 0 psig compared with 500 psig. The para/meta ratio of DIPB was not influenced by pressure.

Data from the foregoing Examples also demonstrates the effect of temperature. Runs were made in the 150–300° C. temperature range. As expected, conversion increased significantly with increases in temperature. Propylene is relatively reactive over the catalyst. Undesired by-products which consume this starting material are formed at the higher temperatures. By using higher cumene/propylene feed ratios (or a multiple bed reactor to achieve this effect), more efficient propylene use could be realized.

One of the primary effects of temperature is to change the para/meta isomer ratio of the DIPB product. At lower temperatures, 150–200° C., the para isomer is favored, p/m is about 78/20. At 250 and 300° C., the p/m ratios are 33–38/67–62.

Data from the foregoing Examples also demonstrates the effect of impregnations with aqueous solutions of magnesium or phosphorous salts followed by calcination. A catalyst was prepared which contained 2.3% magnesium, present as the oxide, on ZSM-12 and tested for preparation of DIPB. Results are summarized in Table 4. Relatively high amounts of para isomer in the DIPB product (81–82%) were observed. Similar results were observed with phosphorus (82% p-DIPB), Table 6, and a combination of Mg and P (86% p-DIPB), Table 5. Excellent selectivity to total DIPB was also observed with P-ZSM-12 and Mg-ZSM-12. As expected, cumene conversion was reduced by impregnation with Mg or P.

Perhaps other impregnation reagents with metal cations larger in size than Mg or P could achieve higher para-selectivity, e.g., to produce 90% or more para isomer in the DIPB product at practical conversions.

Data from the foregoing Examples also demonstrates the effect of steaming of the ZSM-12 catalyst. One sample of HZSM-12, Table 3, was steamed for 7 hours to an alpha=30. Tables 1 and 2 relate to unmodified catalysts with a higher silica/alumina ratio (213/180). Except for somewhat lower cumene conversion, similar performance was observed for these three catalysts in all categories.

Data from the foregoing Examples also demonstrates how the selection of a particular ZSM-12 catalyst can effect the relative yield of diisopropylbenzene.

The para-diisopropylbenzene product of the foregoing Examples may be oxidized, e.g., with air, to the corresponding dihydroperoxide and rearranged by an acid catalyst to hydroquinone and acetone. The meta isomer is converted to resorcinol and acetone by an analogous process.

What is claimed is:

1. A process for the selective propylation of cumene with the selective production of meta-diisopropylbenzene and para-diisopropylbenzene, said process comprising contacting mixtures of cumene and propylene with a ZSM-12 catalyst under sufficient propylation conditions.

* * * * *

UNITED STATES PATENT AND TRADEMARK OFFICE
CERTIFICATE OF CORRECTION

PATENT NO.  : 4,822,943
DATED       : April 18, 1989
INVENTOR(S) : George T. Burress It is certified that error appears in the above-identified patent and that said Letters Patent is hereby corrected as shown below:

```
Col. 1, line 33, "keown" should be --Keown--.
Col. 1, line 43, "N/M2" should be --N/m2--.
Col. 2, line 22, "rations" should be --ratio--.
Col. 2, line 28, "stem" should be --steam--.
Col. 2, line 42, "Linda A" should be --Linde A--.
Col. 6, line 68, "OR" should be --or--.
Col. 7, line 42-43, "incorporaiton" should be --incorporation--.
Col. 12, line 11, "Example 3" should be --Example 5--.
Col. 14, line 46, insert --(i.e. HZSM-12)-- after "ZSM-12".
Col. 15, line 24, "signficantly" should be --significantly--.
Col. 9-10, Table 1, line 1, "22" should be --225--.
Col. 15-16, Table 8, line 14, under "Col. 2" the row where
      "78.2" appears, insert --77.6-- & move each other
    number in that row over one column to the right.
```

Signed and Sealed this

Thirtieth Day of January, 1990

*Attest:*

JEFFREY M. SAMUELS

*Attesting Officer*   *Acting Commissioner of Patents and Trademarks*